United States Patent [19]

Schwebel et al.

[11] 4,338,980
[45] Jul. 13, 1982

[54] DEVICE FOR FILLING MEDICAMENT INJECTORS

[76] Inventors: Paul R. Schwebel, 44045 15th St. West, Lancaster, Calif. 93534; Manuel N. Friend, 311 Bruce La., Turlock, Calif. 95380

[21] Appl. No.: 111,939

[22] Filed: Jan. 14, 1980

[51] Int. Cl.³ .................................................. B65B 3/32
[52] U.S. Cl. ................................ 141/18; 141/311 R; 141/369; 141/375
[58] Field of Search .............. 128/207.24; 141/18–27, 141/1, 2, 369, 378, 113, 311 R–368, 392, 375; 222/46, 47, 48, 41, 50; 137/845

[56] References Cited

U.S. PATENT DOCUMENTS

| 1,052,492 | 2/1913 | Lindsay | 141/378 X |
| 2,644,663 | 7/1953 | Klinger | 137/845 X |
| 3,729,031 | 4/1973 | Baldwin | 141/2 |

Primary Examiner—Frederick R. Schmidt
Attorney, Agent, or Firm—Robert Louis Finkel

[57] ABSTRACT

Either a pyrotechnic-powered needleless injector or (with spacer adapters) a conventional syringe is held in firmly abutting alignment with a dispensing orifice of a special storage vial. A flexible perforated seal forms a plug in the dispensing orifice, opens under liquid pressure to dispense medicament from vial to injector, and seals around the dispensing path between vial and injector against loss of the medicament. The liquid medicament is forced through the orifice under the action of a plunger forming one wall of the vial. The plunger in turn is driven by a micrometer-type screw whcih is calibrated in terms of dispensed volume.

14 Claims, 8 Drawing Figures

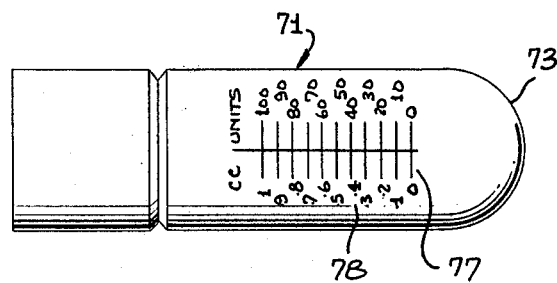
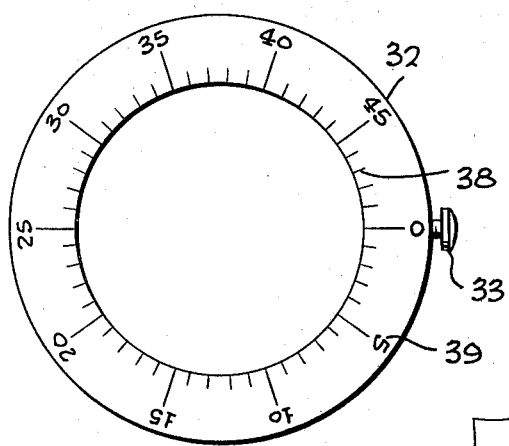
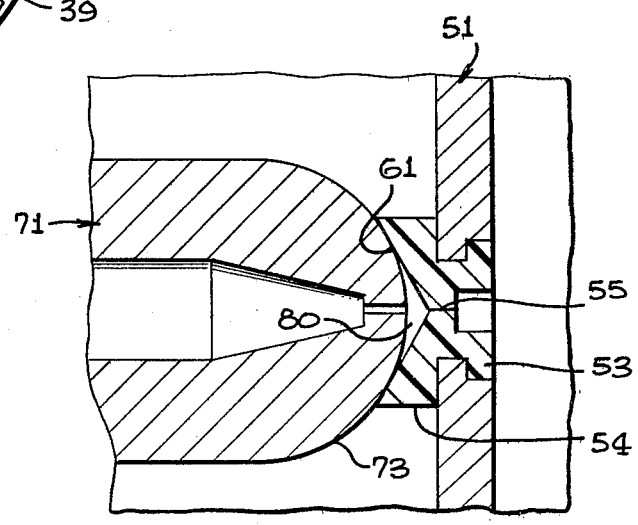
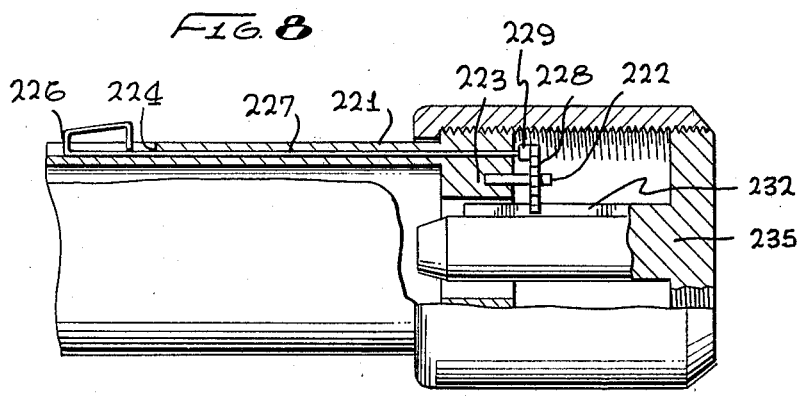

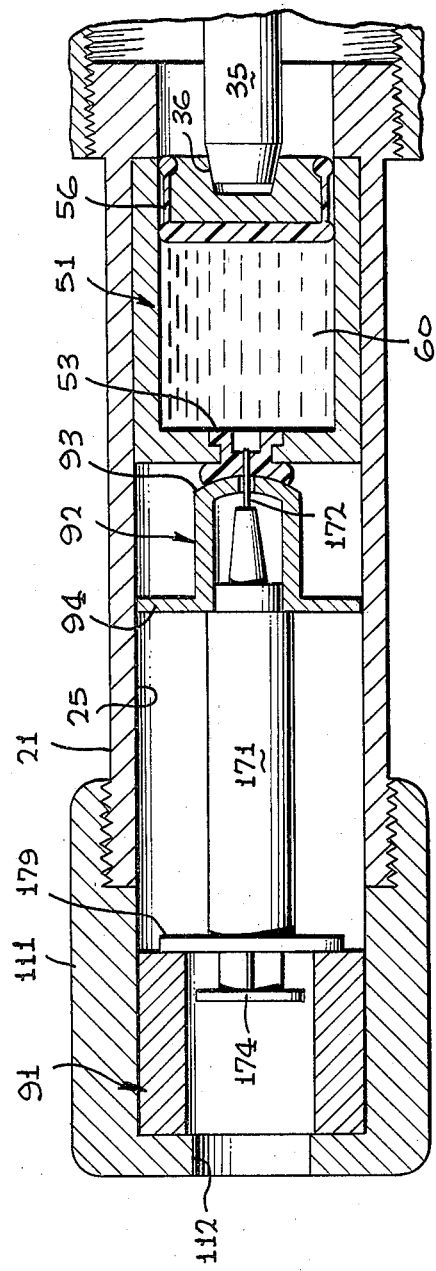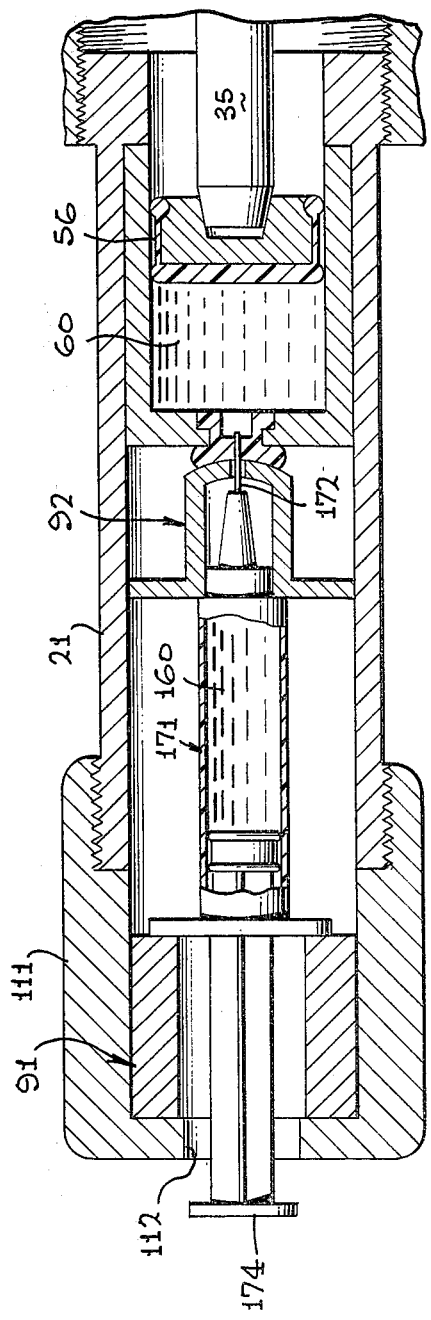

DEVICE FOR FILLING MEDICAMENT INJECTORS

BACKGROUND OF THE INVENTION

1. Field of the Invention

This invention relates to medicators for effecting injections of medicaments and the like, particularly by the use of needleless pyrotechnic-powered injectors but also by the use of conventional syringes.

More particularly, the invention relates to a device for rapidly and easily but very accurately filling such medicators with medicament.

The invention is particularly directed toward use by lay people who are not medically trained and who may, by infirmity due to old age or otherwise, not have full muscular control for fine movements or sharp vision for reading fine volume-calibration scales as on syringes—but who must nevertheless regularly medicate themselves by injections at home. Elderly diabetic outpatients constitute a particularly numerous example.

The invention is also particularly directed toward use by medical professionals for certain specialized applications:

(1) filling needleless injectors, or disposable ampules for such injectors—because neither the injectors nor the disposable ampules are adapted for suction filling as are syringes;

(2) filling syringes in circumstances requiring extremely precise dosages or very precise mixing of different medicaments within a single syringe; and (3) filling needleless injectors, disposable ampules, or syringes with medicaments which are unstable in solution and must be ready-mixed at the time of use.

Examples of medicaments mentioned in the third category are the many lyophilized solutes to which a diluent is added just before use. Further, readily soluble medicaments might be marketable in a dry storage form to enhance shelf life and diminish reactivity problems—and immediately before use dissolved and by means of the present invention loaded into an injection device.

Needleless injectors and disposable ampules are preferably fillable from bulk supply by some procedure which is not limited to a factory or specially equipped laboratory. In particular it is desirable that the device be conveniently fillable by shut-in patients at home, pharmacists in neighborhood dispensaries, paramedics, country doctors, wilderness rescue teams, physicians serving battlefield camps, disaster areas or primitive societies, and other remote users.

2. Prior Art

We know of no prior devices for performing the filling operation described above under the particular constraints mentioned.

Hypodermic syringes of the many sorts with which our invention would be compatible are of course thoroughly familiar devices. Needleless pyrotechnically powered injectors are much less familiar articles to the general public, but are becoming well-known to medical professionals; the state of the art as to such devices may be noted by reference to our U.S. Pat. Nos. 4,089,334, which issued May 16, 1978 under the title "Pyrotechnically Powered Needleless Injector," and 4,124,024, which issued Nov. 7, 1978 with the title "Disposable Hypodermic Injection Ampule."

The first of these patents discloses an integral injecting device accommodating an aliquot or dose of medicament, a pyrotechnic or deflagratory charge capable of propelling the medicament through a fine orifice into a patient, a piston for isolating the medicament from the charge, means for igniting the charge, and a housing which brings the various components together in appropriate relationships.

The second of our patents discloses a modification in which the medicament, pyrotechnic charge and piston are in a separate, disposable module, referred to as an "ampule."

The filling procedure normally used for syringes is not only (as already mentioned) inapplicable to needleless injectors or their disposable ampules; it also has serious limitations even as used for syringes. Hypodermic syringes are conventionally filled by immersing the end of the needle in the medicament and pulling the handle outward, while observing the fluid level in the syringe against the volume scale on the syringe wall. This operation requires a certain amount of manual dexterity or at least steadiness, as well as visual acuity.

The present invention makes pyrotechnic injectors and ampules conveniently fillable in homes, pharmacies and field use; and greatly facilitates the refilling of conventional syringes of virtually any type.

BRIEF SUMMARY OF THE INVENTION

Our invention provides an easily manipulated housing for easily holding both the injector to be refilled and a storage vial of medicament. To align the injector and vial in precisely correct mutual position for filling, the user merely secures them together in the housing, closing the housing with a cap provided.

The user then manipulates a volume-calibrated handle to obtain an indication that the desired volume has been transfered, and removes the injector from the housing. The vial may be left in the housing for use in later refillings of a different injector; alternatively, if the user desires to transfer a quantity of a different medicament into the same injector (or a different injector), the partially empty vial may be temporarily removed from the housing and replaced by a different vial containing the desired other medicament.

The storage vial of our invention has a dispensing orifice at one end, sealed by a perforated flexible plug. The shape of the plug is selected to cooperate with the tip of the injector to be filled (particularly a needleless injector) so that when the housing cap firmly presses the injector tip against the plug the perforation in the plug tends to open, but does not actually open until the user begins to manipulate the dispensing handle. The storage vial is made to be variable in volume, and the variability is linked to the position of the dispensing handle. For example, in a preferred embodiment the interior of the vial is cylindrical, and one wall is formed as a cylindrical piston which slidingly seals against the cylindrical interior of the vial. The piston is linked to the dispensing handle.

The handle is designed as a micrometer screw, and suitable indicia are provided on the housing and the movable handle to permit the user to determine when appropriate amounts have been transferred.

The principles and features introduced above, and their advantages, may be more fully understood from the detailed disclosure hereunder, with reference to the accompanying drawings, of which:

BRIEF DESCRIPTION OF THE DRAWINGS

FIG. 3 is an end (longitudinal) elevation of one component of the structure of FIG. 1.

FIG. 4 is a lateral elevation of the exterior of another component which is shown in cross-section in FIG. 2.

FIG. 5 is an elevational cross-section similar to FIG. 2 but greatly enlarged and showing only a limited portion of the structure of FIG. 2, and in a very slightly different condition.

FIGS. 6 and 7 are elevational drawings in cross-section, representing an alternative embodiment to that of FIGS. 1 through 5.

FIG. 8 is likewise a cross-sectional elevation, representing somewhat schematically yet another alternative embodiment.

DESCRIPTION OF PREFERRED EMBODIMENTS

Figure 1:
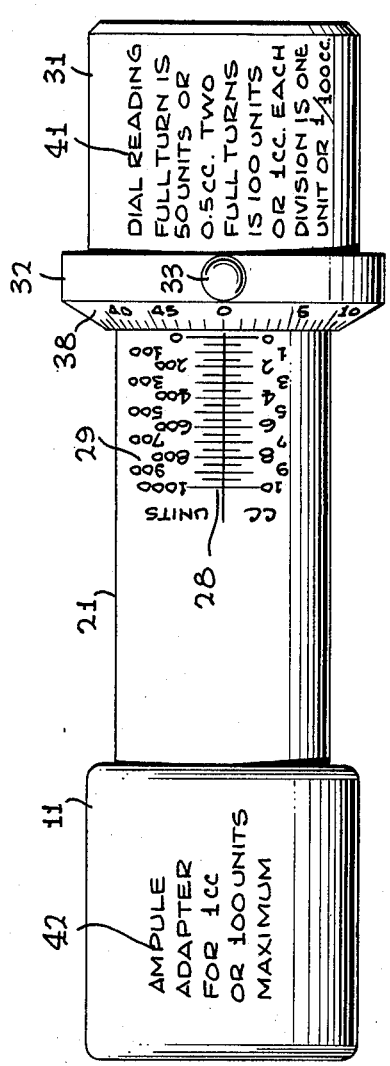
FIG. 1 is an elevational drawing of a preferred embodiment of our invention, showing the exterior of the generally cylindrical structure in a side (radial) view.
Figure 2:
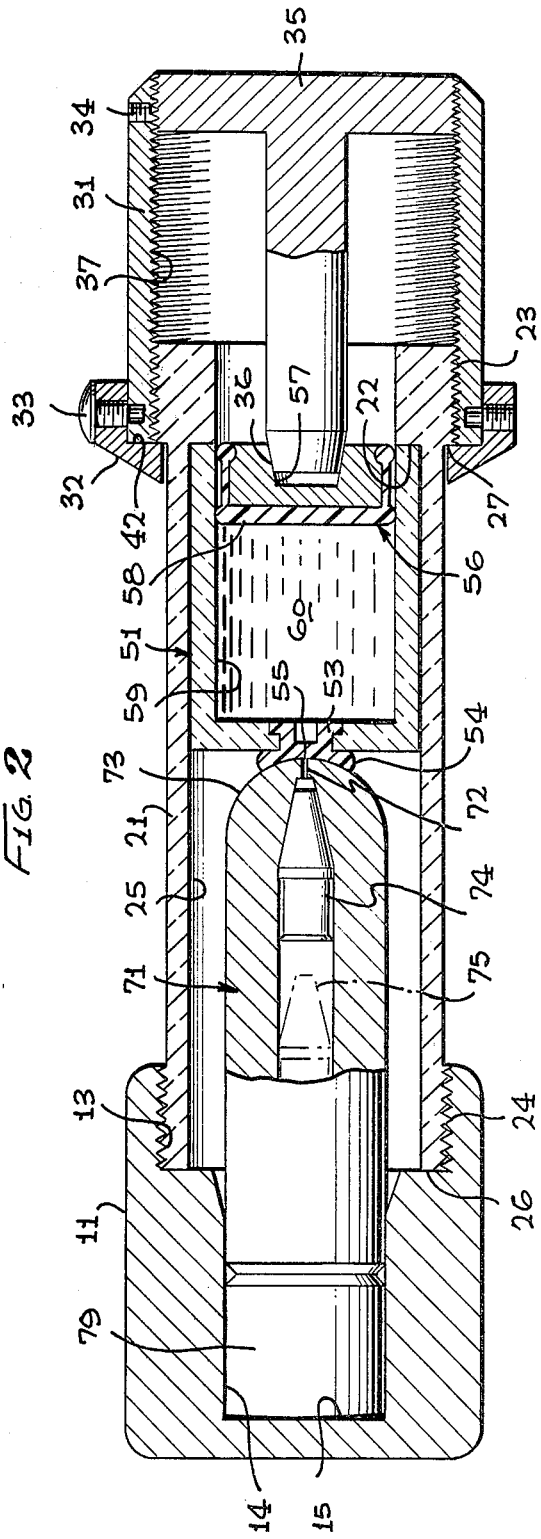
FIG. 2 is an elevational view of the same embodiment, mostly in cross-section, taken along the lines 2—2 of FIG. 1.

As shown in FIGS. 1 through 3, a case or housing 21 is substantially cylindrical, with cylindrical inner and outer shoulders 22 and 27 at one end and a simple cutoff planar termination 26 at the other end. Fine micrometer-quality external threads 23 are provided at the former end, and coarse external threads 24 at the latter.

An internally threaded cylindrical handle 31 is mated to the threads 23, and retained by a keeper ring 32 which is secured to the handle 31 by at least one lock-screw 33, which engages an external groove in the end of the handle 31 as illustrated. The inside face 42 of the keeper ring 32 engages the outer shoulder or flange 27 of the housing 21 to prevent inadvertent unthreading of the handle 31 from the threads 23. The lock-screw 33 may be a knurled-head type to facilitate loosening for rotation of the keeper ring 32, which as explained in detail below provides a fine-calibration function.

A combination end-cap and dispensing ram 35 is threaded into the fine threads 37 in the end of the handle 31, and secured thereto by means of at least one recessed Allen-type set-screw 34.

A dispensing vial 51, having a cylindrical outer wall which fits easily within the inner cylindrical surface 25 of the housing 21, is positioned against the inner shoulder 22 at the fine-threaded end of the housing 21. This vial is initially filled with medicament 60. One end of the dispensing vial 51 is a movable wall or piston 56, having a bearing surface 57 which mates with a bearing surface 36 provided at the end of the dispensing ram 35. The piston 56 carries a sliding seal 58 which mates with the inner cylindrical surface 59 of the vial 51. Fitted into a dispensing aperture in the other, fixed end wall of the vial 51 is a perforated flexible plug 53. This plug is normally self-sealing, to prevent undesired loss of liquid medicament 60 through the perforation 55. However, the peripheral annular portion 54 of the plug, on the outside of the vial wall 51, when deformed in a particular fashion to be described shortly tends to release the seal of the perforation 55.

An end-cap 11 having internal threads 13 is adapted to mate with the coarse-threaded end of the housing 21, and to receive and carry in a reduced-diameter end bore 14 a needleless deflagrant-powered ampule 71. A user, by inserting the deflagrant-retaining end 79 of the ampule 71 into the bore 14 of the end-cap 11, and then screwing the end-cap 11 into place on the coarse-threaded end of the housing 21, can easily and precisely position and align the ampule dispensing orifice 72 with the dispensing perforation 55 of the vial 51 within the housing 21. What is more, the length of the housing 21, between end-surface 26 and shoulder surface 22, is chosen in cooperation with the distance between the bottom 15 and shoulder 12 of the end-cap bore 14, and the overall lengths of the ampule 71 and vial 51. These four dimensions are so chosen that when the end-cap 11 is screwed on with its shoulder 12 firmly in contact with the end-surface 26 of the housing 21, the "nose" 73 of the ampule 71 is pressed with adequate but not excessive force against the sealing plug 53.

It is important that this force be within a suitable range to obtain proper action of the flexible plug, and prevent breakage of the vial 51. As illustrated in FIG. 5 the frontal, mating surface of the plug 53 is conical, with the apex of the concave cone at the central perforation 55. When the semispherical nose 73 of the ampule first contacts the plug a small air gap 80 remains at the center of the plug—that is, at the apex/perforation point. When the ampule is pressed more forcefully against the plug there is no air gap, and the peripheral outer areas of the conical structure are compressed. In addition to forming an effective seal about the periphery of the perforation, to prevent loss of the fluid medicament during transfer, this compression produces stresses within the material of the plug tending toward opening of the perforation 55. However, the perforation does not actually open until the medicament 60 is placed under pressure by operation of the handle 31 and dispensing ram 35 (FIGS. 1 and 2) against the piston 56. Upon application of such pressure the perforation opens easily and the liquid medicament flows readily into the ampule 71. We have found that this action of the flexible plug 53 is optimized by providing an angle of approximately 30 degrees between the conical surface 61 and the planar wall 51 of the vial, using a standard medical-grade rubber for the plug.

As the dispensing handle 31 is operated to force the liquid 60 into the ampule 71 via its own dispensing orifice 72, the dispensing piston 74 within the ampule 71 is moved back by the liquid pressure to a position such as that shown in the broken line at 75 in FIG. 2. As the user manipulates the handle 31 he or she watches the scales 38 and 28, and the numerical indicia 39 and 29, provided on the outside of the keeper ring 32 and housing 21; and stops when the desired incremental volume has been loaded into the ampule 71. Additional indicia (not shown) on the outside of the housing cooperate with the scale 38 to provide a true vernier readout, for use in situations demanding extremely precise filling—as for example when mixing a plurality of medicaments in a single injector, where very accurate proportions are required. To aid in verifying proper charging of the ampule, the housing 21 may be constructed partly or entirely of transparent material, so that the motion of the piston 74 within the ampule 71 may be observed during filling. The vial 51 may also be made transparent, to facilitate monitoring of the quantity of liquid 60 remaining. The scale 77 and numerical indicia 78 on the outside of the ampule 71, as shown in FIG. 4, may also be observed during filling if the housing 51 is made transparent. However, while all of these advantages are present, they are minor and can be dispensed with if it is preferred for other reasons to make the housing 51 opaque; the primary advantages of our invention result from the other provisions described.

The scales 28 and 38 and numerical indicia 29 and 39 are of course exemplary only; it is possible to provide calibration markings as appropriate for any set of design dimensions selected, though the exemplary ones illustrated in FIGS. 1 and 3 are convenient and readily comprehensible. The additional indicia 41 and 42 are also helpful. The housing 21 is typically 1⅜ inch in diameter, and the device at maximum extension is just under 7 inches long. Thus all of the indicia indicated are readily legible even where a certain amount of vision defect is present, and the device itself is a convenient and comfortable size to handle and use—all important considerations.

The vial 51 is advantageously of medical-grade glass (approved by the Food & Drug Administration for storage), and the piston seal 58 of medical-grade rubber.

After the user has transfered the desired amount of medicament to the ampule, he or she unscrews the end-cap 11 and withdraws it with the ampule 71, and inserts the ampule into the firing holder (such as described in our aforementioned patents) for use.

FIGS. 6 and 7 illustrate a slight variant on the device of FIGS. 1 through 5. The principal difference in the fixture itself is that the end-cap 111 in the variant has an aperture 112 sized to permit passage of a syringe handle 174. This modification will not prevent use of the device with a needleless ampule 71 as in FIGS. 1 through 5. As shown in FIGS. 6 and 7, however, this modification in combination with simple spacers 91 and 92 permits use of the filling device of our invention to fill hypodermic syringes 171. The spacer 91 engages hypodermic flange 179, at such a position that the hypodermic needle 172 just enters the vial 51 through perforated plug 53, but does not extend so far into the vial 51 as to interfere with the stroke of piston 56. Spacer 92 has a "nose" 93 which in effect simulates the action of the ampule nose 73 against the flexible seal 53, as described in conjunction with FIG. 5; spacer 92 also has flange 94 which fits easily within the inner cylindrical surface 25 of cylindrical housing 21, to properly center the syringe 171 within the housing 21—so that the needle 172 does not miss the aperture in the plug 53. Characteristics of the dispensing handle, ram 35 and driving surface 36 are the same as described previously for use with a needleless ampule. Of course, as shown in FIG. 7, when a substantial quantity 160 of liquid medicament 60 is transfered, the syringe handle 174 protrudes through aperture 112.

FIG. 8 illustrates part of yet another embodiment of our invention. This embodiment is intended for use of individuals whose sight is extremely poor, or who may be nervous or apprehensive or readily confused in reading scales or numerical indicia; the embodiment of FIG. 8 is operable almost entirely by "feel." Here the ram shaft 235 carries a vane 232 which extends radially from the shaft all along one side. With each rotation of the shaft 235 the vane 232 advances a star wheel, or gear, 228 which is mounted by shaft 222 to the enlarged end shoulder 223 of the housing 221. A smaller vane 229 attached to one tooth or point of the star wheel 228 engages the tip of a control pin 227, and thus prevents further rotation of the ram shaft and dispensing handle, whenever the star wheel 228 makes one full revolution; this occurs every time the ram shaft 235 makes a number of revolutions equal to the number of teeth or points on the star wheel 228. The control pin thus stops the advance of the ram shaft whenever the user turns the handle a number of times equal to the number of teeth on the wheel 228.

The user may disengage this stop mechanism later, to permit beginning another filling operation, by sliding the control pin 227 away from the small vane 229. The user has access to the pin 227 for this purpose where its formed end 226 protrudes outside the housing 221 through groove 224. The control pin slides axially in a hole within the wall of the housing 221; it is shown in the retracted position.

The schematic nature of FIG. 8 may be inferred from the fact that necessary spring-loading of the control pin into engagement with the star-wheel vane 229, and desirable provision of a simple pawl to prevent backward motion of the star wheel 228 between impulses of the large vane 232, are not illustrated. It will also be apparent that the shape of vane 232 and wheel 228 must be carefully selected—and the number of teeth on the wheel 228 also appropriately chosen—to obtain smooth operation and provide a stop action corresponding to a rated volume aliquot to be transfered. With a device of this sort, a pharmacist, physician or medical-supply equipment manufacturer simply provides the patient with a particular unit rated for the dosage which the patient is to take. Possibly the star wheel could be made readily interchangeable by a pharmacist or medical technician, so that it would not be necessary to stock a large variety of complete devices. A more-sophisticated mechanism could be substituted providing selectable but preset rotation counting, so that a single device could be used for different dosages when suitably preset by a person with the necessary mechanical aptitudes and physical condition, without imposing such requirements on the patient on a daily-dose basis.

In all of the devices described in this disclosure, various engineering choices and detail design decisions must of course be made. For example, with respect to the device of FIG. 8 it is necessary to design the mechanism in such a fashion that the pawl mentioned earlier can be disengaged while the dispensing handle is screwed outward to accommodate a new, full vial—and so that the dispensing action then starts out at the beginning of a dose when the dispensing ram is just first engaged with the dispensing piston of the vial. With respect to the devices of FIGS. 1 through 7, similarly, it is necessary to arrange for the various indicia to start out precisely at zero when the dispensing ram is just first engaged with the piston in the vial. There are various ways to accomplish this, as for instance setting all the manufactured filling devices exactly identically and loading all the dispensing vials also exactly identically. Alternatively, certain users could be relied upon to make adjustments of the end-cap and ram 35 with respect to the handle 31, or the keeper ring 32 with respect to the handle 31, upon starting use of a new dispensing vial 51—and thereby gain a cost advantage through use of a less precisely constructed and/or filled vial 51. All of these considerations will, in the light of the foregoing disclosure be understood by one skilled in the art of mechanical design.

It will be understood that the foregoing disclosure is exemplary only, and not to be construed as limiting the scope of our invention, which scope is to be ascertained only by reference to the appended claims.

I claim:

1. A front-filling dispenser for introducing liquid medicament into a needleless injector having a tip containing an injection orifice, comprising:
   a vial adapted to contain such medicaments;
   a resilient plug effectively sealing one end of said vial, said plug having a self-sealing passage therethrough and being deformable to conform sealingly with the tip of said injector;
   means releasably positioning said injector with respect to said vial, for bringing the passage in said plug into communication with said orifice and maintaining said plug in sealing contact with said tip;
   means for varying the volume of said vial and thereby forcing said medicament through said passage and orifice; and
   manually manipulable means, precisely calibrated in terms of medicament volume, for operating said volume varying means and thereby controlling the volume of medicament transfered from said vial into said injector.

2. The dispenser of claim 1 wherein said plug is formed of rubber.

3. The dispenser of claim 1 wherein said plug has a recessed exterior face.

4. The dispenser of claim 3 wherein said face is generally conical and said passage is formed at the apex.

5. The dispenser of claim 3 wherein said volume-varying means comprises a piston movably disposed in said vial at the end thereof opposite said plug.

6. The dispenser of claim 5 wherein said positioning means comprises:
   a casing adapted to retain said vial in one end thereof and to receive said injector in the opposite end thereof; and
   manually operable means acting between said casing and said injector, urging said tip into sealing contact with said plug.

7. The dispenser of claim 6 wherein said manually operable means comprises a cap releasably attached to said opposite end of said casing, said cap being adapted to position said injector with said orifice in communication with said passage.

8. The dispenser of claim 7 wherein said cap is threaded onto said casing.

9. The dispenser of claim 7 wherein said cap is closely conformed interiorly to the shape of said injector.

10. The dispenser of claim 7 wherein said manually manipulable means comprises a handle mounted to said one end of said casing for operative engagement with said piston.

11. The dispenser of claim 10 wherein said handle comprises a micrometer screw threaded to said casing and calibrated with respect to said casing.

12. The dispenser of claim 11 comprising volume indicating markings on said handle and said casing for ascertaining the amount of medicament contained in said vial.

13. The dispenser of claim 12 in combination with a medicament contained in said vial.

14. The dispenser of claim 6 adapted for use with a syringe having a needle extending outwardly of one of its ends, comprising:
   an adaptor positionable in said casing adjacent said vial, said adaptor having a protruberance at one end thereof having an opening therein adapted to permit said needle to extend therethrough, and being formed at the other end thereof to receive and retain the needle-bearing end of said syringe with said needle extending through and outwardly of said protruberance in registry with said passage, said manually operable means being adapted to urge said protruberance into spacing contact with said plug, thereby forcing said needle a predetermined distance into said passage.

* * * * *